United States Patent [19]

Burkhardt et al.

[11] Patent Number: 4,909,339

[45] Date of Patent: Mar. 20, 1990

[54] WEIGHT AND PRESSURE MEASURING DEVICE

[76] Inventors: Michael Burkhardt, Eschersheimer Landstr. 40, 6000 Frankfurt 1; Hans-Ulrich Augustin, Bornstr. 22, D-3052 Bad Nenndorf, both of Fed. Rep. of Germany

[21] Appl. No.: 299,758

[22] Filed: Jan. 23, 1989

[30] Foreign Application Priority Data

Jan. 21, 1988 [DE] Fed. Rep. of Germany ....... 3801656
Jan. 21, 1988 [DE] Fed. Rep. of Germany ....... 3801657

[51] Int. Cl.4 .................. G01G 5/04; G01G 21/00
[52] U.S. Cl. ..................................... 177/208; 177/126
[58] Field of Search ..................... 177/126, 127, 208

[56] References Cited

U.S. PATENT DOCUMENTS 3,305,036 2/1967 Walters ..................... 177/208 X
3,985,191 10/1976 Wellman ........................ 177/208
4,002,216 1/1977 Solow ............................. 177/208
4,537,266 8/1985 Greenberg ..................... 177/208

Primary Examiner—George H. Miller, Jr.
Attorney, Agent, or Firm—Allegretti & Witcoff, Ltd.

[57] ABSTRACT

A weight and pressure measuring device, comprising a fluid filled cushion pad of limited volume, connected to a pressure indicator to measure the pressure produced during pressure loading. Such a measuring device requires little space, is lightweight, and can easily be transported and used. A blood pressure and weight measuring device has an inflatable sleeve which is connected through a tube connection, with a pump device and a pressure measuring device. In order to measure blood pressure as well as weight, by means of such a measuring device, a second inflatable device, with a limited volume, is connected with the pressure measuring device and the pump device. The device measures the pressure produced by the weight load, which is proportional to the weight being determined.

3 Claims, 1 Drawing Sheet

WEIGHT AND PRESSURE MEASURING DEVICE

BACKGROUND OF THE INVENTION

The invention relates to a weight and pressure measuring device.

It is known that there is frequently a relation between blood pressure and weight. During regular examinations of blood pressure, it is therefore highly desirable to also check the weight.

THE PRIOR ART

Various weight measuring devices are known which operate in accordance with various measuring principles, such as, for example, devices in which a comparison of the weights is carried out with scale units, or devices in which the weight force is measured, for example, with spring-type scales.

OBJECTS OF THE INVENTION

The object of the present invention is to provide a weight and pressure measuring device having low space requirements, light weight, and which is easy to transport and use.

A further object is to provide a measuring device by which both blood pressure and weight can be measured in a simple and easy manner. The measuring device should be easy to transport and use anywhere, without difficulty.

THE INVENTION

The measuring device in accordance with the invention has the advantage that it fits, within travelling luggage, and handbags or similar containers, and can therefore be used at any time, independently of location. The measuring device can also be used as a small scale and, in modified form, as a large scale for heavier weights.

The measuring device may be advantageously used by high-blood pressure patients, who must continuously check both blood pressure and weight, a considerable convenience, particularly during longer trips. Both measurements can therefore be carried out reliably and independently of location. The measuring device is light in weight, and requires little space, so that it can be carried within travelling luggage easily and without problem.

THE DRAWINGS

The invention will now be described in greater detail in connection with the drawings, in which FIG. 1 is a diagrammatic illustration of a first form of the weight and pressure measuring device of the invention.

DETAILED DESCRIPTION

Figure 1:
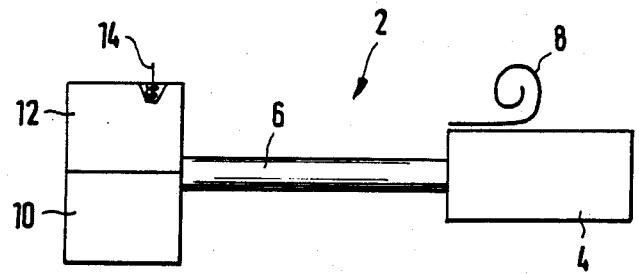

FIG. 1 illustrates a weight and pressure measuring device 2 with a container 4 which has a closed or limited volume, and can be filled with fluid, i.e. gas or liquid. The container 4 may be a cushion pad connected by means of a tube 6, with a manometer 10, as well as with a pump device 12 for inflating the cushion pad 4 and for releasing the pressure. The cushion pad 4 may be provided with a stepping pad 9 which can be rolled up, in order to increase the solidity of the support for the object to be weighed. The pumping device 12 is preferably provided with a zero point indicator 14 for the zero point adjustment of the manometer. The indicator may be a scale, marker, gauge or the like, for reading the pressure-weight, and which can be set at zero.

The zero point adjustment can be made by inflating device 10 until the pressure measuring indicator reaches a predetermined zero mark.

The manometer scale can be directly calibrated in weight indicia. When the cushion pad 4 is loaded with the weight of a person, the manometer 10 reacts to the pressure thereby produced. The weight, which is proportional to the pressure produced, can be read directly off the manometer scale.

The device 12 preferably consists of an air pump. The cushion pad 4 can be filled with a liquid or partially filled with a liquid and partially with air or another gas. A partial filling with liquid and with gas provides the advantage that the pressure can be measured in the gas portion, which, from the viewpoint of stability, is of particular advantage.

Apart from pressure measuring devices which operate purely mechanically, electro-mechanical transformers can also be used, which employ, for example, changes in capacitance or resistance in order to measure the pressure or weight.

Figure 2:
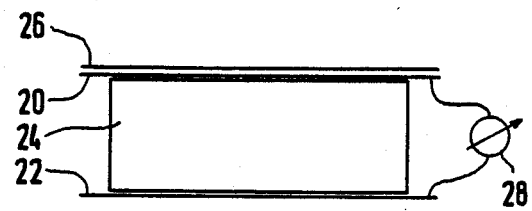
FIG. 2 is a similar diagram of another form of the weight and pressure measuring device.

The application of the principle of capacitance change is depicted in figure 2. Two conductive foils, between which a compressible dielectric 24 is located, are used as condenser plates 20, 22. A stepping pad 26 of electrically insulating material is placed on the upper foil 20 which ensures that the compression of the dielectric takes place in a uniform manner if the lower foil 22 is placed on an even surface. Through the compression of the dielectric due to loading, the capacitance changes, which change can be measured on the measuring gauge 28, and which provides a measurement for the weight load. The measuring device in FIG. 2 can be selected from a very wide range of scales which are economical in weight and space as well as transportable. Apart from individual and small scales, large-surface transportable scales can also be used which can be applied anywhere, rapidly and without great expense. In the framework of traffic inspections, for example, a foil field may be spread out on a highway. The weight of vehicles passing over it can be indicated directly, so that it can be immediately determined whether or not the vehicle is overloaded. Such a measuring device also makes it possible to determine weights or forces at different locations, and on large surfaces.

For the second principle of measurement (change in resistance), which is not depicted here, a second, closed gas-filled system can be provided in communication with a closed, gas-filled system. When the first, external system is loaded with a weight, the pressure in its interior rises. Through this means, the volume of the second system is reduced. This mechanical change can be conveyed to an electrical variable resistor, whereby the change in resistance represents a proportional change in the weight load. The external system can also be filled with liquid, instead of with gas.

Figure 3:
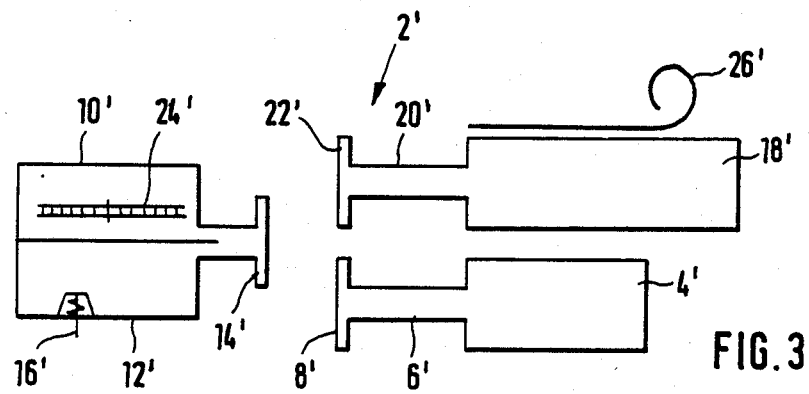
FIG. 3 is a similar diagram of a third form of the measuring device in accordance with the invention.

FIG. 3 of the diagram schematically depicts a measuring device 2' with an inflatable sleeve 4' for blood pressure measurement, which is connected, through a tube 6' and plug connection 8', with a pressure measuring device 10' and a pump device 12', which has a complementary interconnecting plug connection 14'. The pump device is equipped with a zero point indicator 16'. The zero point adjustment can take place, for example, with a spring bar and a calibration mark. The indicator may be a scale, marker, gauge or the like, which canb e set at zero, for reading the weight. Instead of the spring bar, a helical torsion spring (not depicted) can be used.

The zero point adjustment can, however, also take place simply by inflating the device sufficiently to cause the pressure measuring gauge to reach the zero mark, which can be predetermined.

The measuring device 2' furthermore has an inflatable cushion pad 18, which, through tube 20' with a plug connection 22', can be connected with the pressure measuring device 10' and the pump device 12'.

The pressure measuring device 10' includes a scale 24' with a lower measuring range for blood pressure measurements, and an upper range for weight measurements. A stepping pad 26' which can be rolled up may be placed on the cushion pad 18'. The manner of operation of the measuring device in accordance with FIG. 3 is as follows:

By means of the pressure measuring device 10', the pump device 12' and the sleeve 4', the blood pressure, which is read on the low range scale of the pressure measuring device, is measured in the conventional manner. Then the tube 6' of the sleeve is released from the pump device 12' and, in its place, the cushion pad 18, with the tube 20', is connected to the pump device 12' by means of plug 22. The cushion pad is then inflated until the zero point adjustment has taken place. After that, the stepping pad is unrolled onto the cushion pad, on which an individual may then be placed for weight measurement. The weight can then be read off the upper range portion of the scale of the pressure measuring device.

Figure 4:
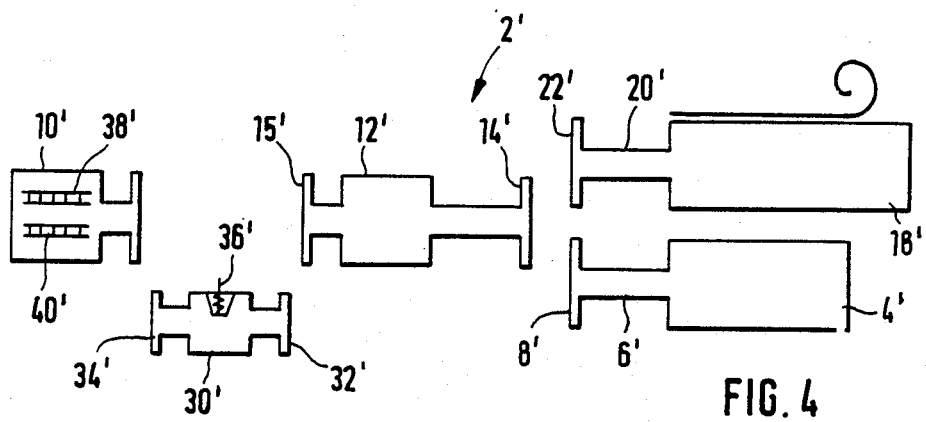
FIG. 4 is a similar diagram of a fourth form of the measuring device in accordance with the invention.

FIG. 4 of the diagram schematically depicts a measuring device 2', which has an inflatable sleeve 4' for blood pressure measurement, equipped with a tube 6' with a plug connection 8'. The measuring device 2' furthermore has a pressure measuring device 10', a pump device 12' for inflating and relieving the pressure, having two interchangeable plugconnections 14' and 15', an inflatable cushion pad 18' with a tube 20' and a plug connector 22'. A stepping pad 26' may be placed onto the cushion pad. A pressure reducing device 30' with two plug connections 32', 34', equipped with a zero point indicator 36' may be connected to measuring means 10' and to fitting 15' of the pump 12' when said pump is connected to the pad 18 at fitting 22'.

The zero point indication or adjustment can take place in the manner of execution in accordance with FIG. 3.

The pressure measuring device 10' has two scales 38', 40', one of which serves for measuring blood pressure, and the other of which serves for measuring the weight.

The manner of operation of the measuring device in accordance with FIG. 4 is as follows:

By means of the interconnected pressure measuring device 10', the pump device 12' and the sleeve 4', the blood pressure, which can be read off one of the two scales of the pressure measuring device, is measured in the conventional manner. Then, the pressure measuring device 10' is disconnected from the pump device and the pressure reducing unit 30' is connected with the pump device and the device 10'. The inflatable cushion pad 18' is connected to the other end of the pump device. Then, the cushion pad is inflated until the zero point adjustment has taken place. After the stepping pad 26' has been placed on the cushion pad, a person can step onto the cushion pad, and the weight of the person can be read directly off the second scale of the measuring device 10'.

Apart from pressure measuring devices operating in a purely mechanical manner, electro-mechanical transformer, which use, for example, changes of capacitance or changes of resistance for the pressure or weight measuring, may also be used.

In the first case, two conducting foils, between which a slightly compressible dielectric is positioned, may be used. This arrangement is used in a closed, gas-filled system. If this system is loaded with a weight, the resulting volume change of the dielectric leads to a change in capacitance, which can be measured, and serves as a measure for the porportional weight load.

For the second measuring principle, a second, closed gas-filled system is provided within a closed, gas-filled system. When the first external system is loaded with a weight, the pressure increases in its interior. By this means, the volume of the second system is reduced. This mechanical change can be communicated to an electrical variable resistor, which senses the change in resistance which is proportional to the weight load. The external system can also be filled with liquid instead of with gas.

One advantage of the electro-mechanical transformer consists in the fact that a savings in weight and space is made possible, relative to mechanical systems.

What is claimed is:

1. A weight and pressure measuring device comprising
    a closed container filled with fluid having a weight supporting surface,
    a blood pressure sleeve,
    a housing containing a pump and a pressure measuring meter for sensing the change in pressure produced by a weight on said weight supporting surface,
    a plug-receiving fitting on said housing communicating with said pump and said meter,
    a tube connecting at one end to said container and having a plug at the other end for detachably connecting to said plug-receiving fitting to provide communication between said container and said meter and pump, and
    a tube connecting at one end to said sleeve having a plug on the other end for detachably connecting to said plug-receiving fitting to provide communication between said sleeve and said meter and pump.

2. The device of claim 1 in which said pressure measuring meter has a scale indicating two pressure ranges, a lower range for measuring blood pressure and a higher range for weight measurement.

3. A weight and pressure measuring device comprising
    a closed container comprising a cushion pad filled with fluid having a weight supporting surface,
    a pressure measuring meter in communication with said container for sensing the change in pressure produced by a weight on said weight supporting surface,
    a pump, pressure reducing means having fittings at both ends for detachably connecting to said pump and to said closed container, and
    a blood pressure sleeve which detachably connects to said pressure reducing means in place of said container.

* * * * *